United States Patent [19]
Watanabe et al.

[11] Patent Number: 5,494,802
[45] Date of Patent: Feb. 27, 1996

[54] TISSUE ANTIGEN AND DIAGNOSTIC METHOD FOR HUMAN OSTEOPOROSIS USING THE SAME

[75] Inventors: Hiroshi Watanabe, Hiki; Mikio Akita, Kawagoe; Kohsei Gotoh, Higashimatsuyama; Kazuyuki Kitamura, Sakado, all of Japan

[73] Assignee: Hoechst Japan Limited, Tokyo, Japan

[21] Appl. No.: 32,634

[22] Filed: Mar. 17, 1993

[30] Foreign Application Priority Data

Mar. 19, 1992 [JP] Japan ................................. 4-063838

[51] Int. Cl.⁶ .................. G01N 33/53; G01N 33/536; G01N 33/541
[52] U.S. Cl. .................. 435/7.92; 435/7.1; 436/501; 436/536; 436/540
[58] Field of Search ................. 530/350; 435/7.1, 435/7.92; 436/501, 536, 540

[56] References Cited

FOREIGN PATENT DOCUMENTS

WO91/10141  7/1991  WIPO.

OTHER PUBLICATIONS

Ramsamooj, et al.; Journal of the National Cancer Institute, vol. 84, No. 8, pp. 622–628; Apr. 15, 1992.
Ran, et al.; The Journal of Biological Chemistry, vol. 267, No. 6, pp. 3618–3625; Feb. 25, 1992.
P. H. Hissey, K. J. Thompson & L. Bawden, "Single-Step Monoclonal Antibody Affinity Purification of Human Urogastrone from Urine," Journal of Immunological Methods, 78:211–216 (1985).
A. Voller, D. E. Bidwell & A. Bartlett, "Enzyme immunoassays in diagnostic medicine", Bull. World Health Organ., 63:55–63 (1976).
B. A. Diamond, D. E. Yelton & M. D. Scharff, "Monoclonal Antibodies, A New Technology for Producing Serologic Reagents," The New England J. Medicine, 304:1344–1349 (1981).
K. Olden & K. M. Yamada, "Direct Detection of Antigens in Sodium Dodecyl Sulfate–Polyacrylamide Gels," Analytical Biochemistry, 78:483–490 (1977).

*Primary Examiner*—Donald E. Adams
*Attorney, Agent, or Firm*—Finnegan, Henderson, Farabow, Garrett & Dunner

[57] ABSTRACT

An animal tissue antigen for osteoporotic patients that reacts with antibody in a serum of human osteoporotic patients, but does not react with that in normal human serum. Preferably, a specific antigen for osteoporotic patients in rat or mouse epithelium of tongue mucous membrane, epithelium of tracheal mucous membrane, upper lip epidermis or follicular epithelium containing upper lip hair shafts, or a specific antigen for osteoporotic patients contained in cultured cells of a human squamous cell tongue carcinoma cell lines such as SCC-9 and fibroblast cell lines such as MRC-5. Osteoporosis can be both specifically and easily diagnosed by bringing the above-mentioned antigen in contact with a serum of a subject and then testing for the presence of an antigen-antibody reaction.

3 Claims, No Drawings

TISSUE ANTIGEN AND DIAGNOSTIC METHOD FOR HUMAN OSTEOPOROSIS USING THE SAME

FIELD OF THE INVENTION

The present invention relates to a tissue antigen that reacts with an antibody particularly existing in a serum of osteoporotic patients. Moreover, the present invention also relates to a novel method for immunochemical diagnosis of osteoporosis by detection of autoantibody to the specific antigen.

DESCRIPTION OF THE PRIOR ART

Osteoporosis is a disease characterized in that bone mineral density is reduced though bone composition is normal. Osteoporosis is seen particularly and frequently in women and postmenopausal osteoporosis is observed at a high frequency accompanying menopause in women of 40 years and older. On the other hand, so-called senile osteoporosis is observed in both men and women starting at 70 years of age. Although clinical symptoms are not especially observed while reduction of bone mineral density is mild, as the extent of that depletion becomes pronounced, bone fractures and deformation begin to occur. In particular, since the predominant site of these fractures is the spinal column, pressure fractures of vertebrae and symptoms of lower back pain due to deformation of the spinal column appear. Moreover, fractures of the neck of the femur and pelvis occasionally deprive patients of movement. Therefore, the establishment of a reliable and simple diagnostic method that allows discovery of osteoporosis as early as possible while also allowing effective treatment is strongly desired.

Current methods employed for diagnosis of osteoporosis are dependent on physical techniques such as X-ray photographs. Not only is this technique both bothersome and time-consuming, it also has the shortcoming of only being able to be used during the latter stages of said disease when reduction of bone mineral density has become conspicuous. Although efforts have been made to detect factors relating to metabolic bone diseases, such as osteocalcin, parathyroid hormone (PTH), pyridinoline and C-terminal procollagen, from blood and urine for use in diagnosis, considerable problems still remain in terms of specificity and sensitivity.

DETAILED DESCRIPTION OF THE INVENTION

Most of the factors related to regulation of bone metabolism (including GM-CSF, TGF-$\beta$, IFN-$\gamma$, TNF and IL-1$\beta$) are produced by cells of the immune system. In addition, these factors are also known to act on cells of the immune system. Moreover, the precursors of osteoclasts are monocytes, and these cells have a role in starting immune reactions. These facts suggest the possibility that abnormalities of the immune system induce osteoporosis.

An interesting fact related to the supposition is that osteoporotic and autoimmune diseases both occur frequently in middle aged and elderly women. In other words, the possibility can be considered that abnormalities of the immune system cause some form of autoimmune reaction which results in the occurrence of osteoporosis. If this supposition is correct, some form of autoantibody to somatic autoantigen ought to be able to be detected from the serum of osteoporotic patients, and this autoantibody ought to be an important indicator for the diagnosis of osteoporosis. Since it is known that autoantigens are typically well preserved in terms of their evolution, autoantibodies in patient serum are expected to be detected even when using animal antigen.

Based on the above hypothesis, the inventors of the present invention have discovered an autoantibody, which reacts with a specific antigen and particularly exists in a serum of osteoporotic patients, by reacting the serum of osteoporotic patients with rat and mouse tissue sections as the antigen and then detecting the bound antibody by immunofluorescence technique.

In the present invention, total body sections of neonatal rats were used for the first time as antigen for the purpose of detecting all autoantibodies having the possibility of being produced in osteoporosis by immunofluorescence technique. As a result, extremely strong immunofluorescence was observed in epithelium of tongue mucous membrane, epithelium of tracheal mucous membrane, upper lip epidermis and epithelial follicles surrounding upper lip hair shafts in about 80% of the sera of osteoporotic patients. This type of strong immunofluorescence was not observed for the same tissues in normal serum. This immunofluorescence was much stronger than that observed in reaction with the sera of systemic lupus erythematosus patients, one of the autoimmune diseases in which autoantibody to cellular antigens is known to be produced in large amounts. Moreover, in the case of the serum of systemic lupus erythematosus patients, the cell nuclei of cells through the entire body are stained, thus demonstrating a clearly different staining pattern.

Although strong immunofluorescence was observed in the limited sites in tissue of the tongue, trachea and upper lip in osteoporosis, these findings have not been previously reported in autoimmune diseases, and are findings that are characteristic to osteoporosis. Similar findings were also obtained in sections of mouse tongue. Moreover, analyses conducted by Western blotting indicated that the target antigen present in the tongue is proteins having a molecular weight of about 70 KD and about 40 KD. It was indicated that this target antigen is not a factor related to regulation of bone metabolism by known BMP (bone morphogenetic protein) or BCF (bone calcification factor) by Western blotting and enzyme-linked immunosorbent assay (ELISA) using purified recombinant human BMP and BCF as antigens. In other words, the sera of osteoporotic patients did not react at all with BMP or BCF. The present invention relates to an antigen specific to osteoporotic patients that is present in animal tissue and reacts with antibody in the serum of human osteoporotic patients, but does not react with that in normal human serum. As a preferred antigen, there can be mentioned an antigen specific to osteoporotic patients from rat or mouse epithelium of tongue mucous membrane, epithelium of tracheal mucous membrane, upper lip epidermis or follicular epithelium containing upper lip hair follicles, or an antigen specific to osteoporotic patients contained in cultured cells of human squamous cell tongue carcinoma cell lines such as SCC-9, human squamous cell tongue carcinoma cell line CRL-1629, purchased from the American Type Culture Collection (ATCC, Rockville, Md., USA), fibroblast cell lines such as MRC-5 or fibroplast cell line CCL-171, purchased from ATCC. Among these examples, the specific antigen to osteoporotic patients contained in the epithelium of tracheal mucous membrane of rats has a molecular weight of about 70 KD and about 40 KD in sodium dodecyl sulfate (SDS) polyacrylamide gel electrophoresis in the reduced condition, while the antigen contained in cultured cells of human squamous cell tongue carcinoma cell line SCC-9 has a molecular weight of about 38 KD.

The present invention relates to antibodies which are obtained by immunization with an antigen existing in animal tissues that reacts with antibody in a serum of human osteoporotic patients but does not react with that in a normal human serum. The present invention in particular relates to polyclonal and/or monoclonal antibodies.

The invention further relates to a process for the preparation of the above-mentioned antibodies and to the use thereof in immunoassays.

The immunization of a species with the above-identified antigen takes place by processes known from the literature (A. Voller (1976) Bull. World Health Organ., Vol 63, pages 55–63; B. A. Diamond (1981) The New England J. Medicine, Vol 304, No. 22, pages 1344–1349).

Moreover, the present invention relates to a diagnostic method for human osteoporosis using an antigen specific to the sera of human osteoporotic patients, the antigen presenting in animal tissue and reacting with antibody in the serum of human osteoporotic patients but not reacting with antibody in normal human serum.

Examples of the detection method includes:

(1) the immunofluorescence of tissue section wherein frozen thin sections of tissue containing these antigens are affixed to a slide glass and serum of the test sample is dropped onto the thin sections to allow to react, and this is further allowed to react with a secondary antibody bound with a fluorochrome group to detect the fluorescence microscopically;

(2) the cell enzyme-linked immunosorbent assay (CELISA) technique wherein cells containing these antigens are fixed into plastic wells and serum of the test sample is added to these wells to allow to react, and this is further allowed to react with a secondary antibody bound with a fluorochrome group to detect the fluorescence with a detector;

(3) the Western method wherein protein in tissue and cell extracts containing these antigens is separated by molecular weight using SDS polyacrylamide gel electrophoresis containing a reducing agent, the protein is transferred from this gel onto a nitrocellulose membrane and this membrane is reacted with serum of the test sample, followed by further reaction with a secondary antibody bound with an enzyme to visually identify the coloring; and (4) the enzyme-linked immunosorbent assay (ELISA) technique wherein tissue extracts or cell extracts containing said antigens or these antigens purified by affinity chromatography using an antibody specific to the serum of osteoporotic patients are fixed into plastic wells, and serum of the test sample is added to these wells to react, followed by further reaction with a secondary antibody bound with an enzyme to detect the color density with a detector.

Each of these assay techniques is well known to those skilled in the art. Examples of literatures to be used as references that provide detailed descriptions relating to typical immunochemical assay techniques, including the tissue section immunofluorescence technique, the CELISA technique, the Western blotting technique and ELISA technique, include Immunological Methods I & II edited by Lefkovits & Pernis (U.S.A., Academic Press, 1979, 1981), Methods in Enzymology, Vols. 70, 73, 74 and 84 edited by Langone & Van Vunakis (U.S.A., Academic Press, 1980, 1981, 1982), and Antibody as a Tool edited by Marchalonis & Warr (U.K., John Wiley & Sons, 1982). In addition, examples of references pertaining to the Western method include the publication of Olden & Yamada (Analytical Biochemistry, Vol. 78, p. 483–490, 1977), while examples of references pertaining to methods for purifying antigens by affinity chromatography using a specific antibody include the publication of Hissey, et al. (J. Immunol. Methods, Vol. 78, p. 211–216, 1985).

The present invention will be described below specifically by way of Examples.

EXAMPLE 1

Immunofluorescence of Rat Frozen Tissue Sections Using Sera From Osteoporotic Patients Neonatal rats were frozen followed by the preparation of longitudinal tissue sections by cutting along the median lines of the body. The sections were affixed to a slide glass and fixed by treating with acetone at room temperature for 5 minutes. After air drying, a serum sample from an osteoporotic patient diluted by a factor of 1:100 with a buffer was spread over the tissue sections to react with all antigens contained in the tissue. After reacting at room temperature for 30 minutes, the serum was washed off with PBS. FITC-labeled anti-human IgG antibody (DAKO A/S, Denmark) was spread over the tissue sections in order to detect human IgG antibody bound to the tissue antigen. After reaction was carried out at room temperature for 30 minutes, excess labeled antibody was washed off with PBS. The sites where antibody was bound were examined by a fluorescent microscope. The parts of luminescence with yellow indicate places at which antigen-antibody reaction has occurred. With respect to the rats, tissue sections were prepared from the tongue and trachea after which the presence of antigen was examined in the same manner as described above. When the sera of osteoporotic patients were reacted with rat total body tissue sections, strong immunofluorescence was observed in epithelium of tongue mucous membrane cells, epithelium of tracheal mucous membrane cells, upper lip epidermal cells and follicular epithelial cells containing upper lip hair shafts. Somewhat weaker immunofluorescence was also observed in the neurons of the spinal column.

The above results suggest that in osteoporosis, large amounts of specific antibody (autoantibody) are produced with respect to antigen present in extremely limited locations in tissue. Similar findings were also obtained by staining experiments using mouse tongue and trachea sections.

As a result of investigating the antibody positive rates for the sera of osteoporotic patients and normal serum using rat tongue sections for the antigen, 8 of 10 specimens were strongly positive for sera from osteoporotic patients, while the remaining two specimens were completely negative. As a result of testing on 11 specimens for normal serum, there were 3 false positives and 8 specimens that were completely negative.

EXAMPLE 2

Preparation of Rat Tongue Tissue Extract

Using the tongues of mature rats as the starting material (rat tongue weight: about 0.3 g/animal), the upper half of this tongue tissue was removed with a scalpel (weight of upper half: about 0.15 g/animal) after which it was cut up as finely as possible with scissors. Moreover, the finely cut up upper half of the rat tongue was transferred to a mortar where it was crushed while dropping in 1 ml of 8M aqueous urea per 0.15 g of the upper rat tongue. When this was ground for about 5 minutes in the mortar until solid portions were no longer observed, a highly viscous liquid was obtained. This liquid was then removed into a centrifuge tube in which it was centrifuged for 5 minutes at 12,000 rpm with a desktop centrifuge. The resulting supernatant was then used as the rat tongue extract.

EXAMPLE 3

Detection of Rat Tongue Tissue Specific Antigen Protein by Western Blotting Technique (I)

To 100 µl of the rat tongue extract obtained in Example 2 was added 100 µl of Tris-SDS sample treatment solution containing 2-mercaptoethanol (2-ME). After mixing well, the mixture was reduced by heating at 80° C. for 10 minutes, and the treated sample was placed on an SDS-PAGE plate having a gel concentration gradient of 10 to 20% so that the amount of treated sample on the plate was 25 µl/cm of gel. Electrophoresis was then performed at a constant current of 30 mA. The power was turned off when the end of the electrophoresis reached a point 5 mm before the end of the gel. A transfer membrane was placed on the gel. After completion of transfer at 60 V for 2 hours in a refrigerator at 8° C., a 1 to 2 cm portion was cut from the end of the membrane and protein staining was performed using Coomassie Brilliant Blue to confirm that the protein extracted from the rat tongue had transferred onto the membrane.

Once transfer of protein had been confirmed, the membrane was immersed in a Tris-buffered saline containing 0.5% casein and allowed to stand overnight at 4° C. (blocking). The blocked membrane was then cut into short strips measuring 4 to 5 mm in width which were then immersed in both patient and normal sera diluted 101 times (10 µl+1,000 µl) with a Tris-buffered saline containing the casein used for blocking. The primary reaction was then carried out at room temperature for 1 hour while shaking. After completion of the primary reaction, the membrane was washed well with a phosphate-buffered saline.

Next, the membrane was immersed in anti-human IgG-peroxidase-labeled antibody (rabbit) (DAKO A/S, Denmark) diluted 101 times with a Tris(hydroxymethyl)aminomethane (Tris) buffered saline containing 0.5% casein. The secondary reaction was then carried out at room temperature for 1 hour while shaking. Following completion of the reaction, a similar washing procedure to that at completion of the primary reaction was performed. A color former [4-chloronaphthol (6 mg/ml) methanol solution/hydrogen peroxide] was then added to the washed membrane to develop color. As a result, a clearly defined, single band having a molecular weight of about 70 KD was detected which was specific to osteoporotic patients.

EXAMPLE 4

Detection of Autoantibody by ELISA Technique

The rat tongue extract obtained in Example 2 was diluted by 50 times with a phosphate-buffered saline and 50 µl aliquots were placed in the holes of a 96 hole microplate. The plate was then left to stand overnight at 4° C. (coating procedure). Next, said plate coated with rat tongue extract was washed three times with a phosphate-buffered saline containing 0.5% Tween followed by the addition of 250 µl aliquots of Tris-buffered saline containing 0.5% casein to each hole (blocking) and allowing the plate to stand at room temperature for 45 minutes. Moreover, the plate was again washed three times followed by the addition of 50 µl aliquots of patient and normal sera diluted by 100 times with a phosphate-buffered saline containing 0.05% Tween and allowing to react at room temperature for 1 hour (primary reaction).

After completion of the primary reaction, the plate was again washed three times with a phosphate-buffered saline containing 0.05% Tween, 50 µl aliquots of anti-human IgG-peroxidase-labeled antibody diluted by 40,000 times with a Tris-buffered saline containing 0.5% casein were added and allowed to react at room temperature for 1 hour (secondary reaction).

Following completion of the secondary reaction, the plate was again washed three times followed by the addition of 50 µl aliquots of substrate solution/color former (chromogen substrate) and allowing to react at room temperature for 30 minutes.

After reaction was carried out for 30 minutes, it was stopped with 0.5N dilute sulfuric acid and the plate was measured at a dominant wavelength of 450 nm and complementary wavelength of 650 nm using a colorimeter. Results were obtained that were similar to those of Example 1.

EXAMPLE 5

Preparation of Human Tongue Carcinoma Cell Extract

Using cultured cells of human squamous cell tongue carcinoma cell line SCC-9 (ATCC, CRL-1629) at a cell count of about $1 \times 10^7$ cells as the starting material, the cells were suspended in about 0.5 ml of a saline and then destroyed by ultrasonic wave treatment for 10 seconds. The supernatant obtained by centrifuging the resulting solution for 10 minutes at 10,000 rpm with a desktop centrifuge was then used as the human tongue carcinoma cell extract.

EXAMPLE 6

Detection of Specific Antigen Protein of Human Squamous Cell Tongue Carcinoma Cell Line SCC-9 by Western Blotting Technique To 0.5 ml of the human tongue carcinoma cell extract obtained in Example 5 was added 0.5 ml of 20% trichloroacetic acid (TCA) solution followed by centrifuging for 5 minutes at 10,000 rpm with a desktop centrifuge. Following centrifugation, 100 µl of a Tris-SDS sample treatment solution containing 2-ME was added to the sediment following by reduction by heating at 100° C. for 3 minutes. 15 µl aliquots of the treated sample were placed in each well of SDS-PAGE plate having a gel concentration gradient of 4 to 20% after which electrophoresis was performed at a constant current of 60 mA.

The power was turned off when the end of the electrophoresis reached a point 5 mm before the end of the gel. After performing transfer for 2 hours at a constant current of 200 mA at room temperature, a portion of the membrane was cut and protein staining was performed using Coomassie Brilliant Blue to confirm that the protein had transferred onto the membrane. Then, the membrane was immersed in phosphate-buffered saline (PBS) containing 3% bovine serum albumin (BSA) and left to stand overnight at 4° C. (blocking). The blocked membrane was then cut up and immersed in both patient and normal sera diluted 100 times. The primary reaction was then carried out at room temperature for 2 hours while shaking.

After completion of the primary reaction, the membrane was washed well with PBS containing 0.05% Tween 20. Next, the membrane was immersed in anti-human IgG-peroxidase-labeled antibody (rabbit) diluted 300 times with PBS containing 1% BSA. The secondary reaction was then carried out at room temperature for 1 hour while shaking. After completion of the reaction, a washing procedure was performed in the same way after the primary reaction. A color former [4-chloronaphthol (6 mg/ml) methanol solution/hydrogen peroxide] was then added to the washed membrane to develop color. As a result, a clearly defined, single band having a molecular weight of about 38 KD was detected which was specific to osteoporotic patients.

EXAMPLE 7

Immunofluorescence of Human Tongue Carcinoma Cells Using Sera From Osteoporotic Patients After culturing and affixing $2\times10^4$ cells of human squamous cell tongue carcinoma cell line SCC-9 onto a slide glass, the cells were fixed by treatment with acetone at room temperature for 5 minutes. After air drying, a serum sample from an osteoporotic patient diluted by a factor of 1:100 with a buffer was spread over the cells to react with all antigens contained in the cells. After reacting at room temperature for 30 minutes, the serum was washed off with PBS. FITC-labeled anti-human IgG antibody was spread over the cells in order to detect human IgG antibody bound to the tissue antigen. After reacting for 30 minutes at room temperature, excess labeled antibody was washed off with PBS. The sites where antibody was bound were examined by a fluorescent microscope. As a result, strong immunofluorescence was observed. The parts of luminescence with yellow indicate places at which antigen-antibody reaction has occurred.

EXAMPLE 8

Detection of Rat Tongue Tissue Specific Antigen Protein by Western Blotting Technique (II)

To 100 μl of the rat tongue extract obtained in Example 2 was added 100 μl of Tris-SDS sample treatment solution containing 2-ME. After mixing well, the mixture was reduced by heating at 100° C. for 1 minutes, and the treated sample was placed on an SDS-PAGE plate having a gel concentration 12% so that the amount of treated sample on the plate was 25 μl/cm of gel. Electrophoresis was then performed at a constant current of 30 mA. The power was turned off when the end of the electrophoresis reached a point 5 mm before the end of the gel. A transfer membrane was placed on the gel. After completion of transfer at 60 V for 2 hours in a refrigerator at 8° C., a 1 to 2 cm portion was cut from the end of the membrane and protein staining was performed using Coomassie Brilliant Blue to confirm that the protein extracted from the rat tongue had transferred onto the membrane.

Once transfer of protein had been confirmed, the membrane was immersed in a Tris-buffered saline containing 0.5% casein and allowed to stand overnight at 4° C. (blocking). The blocked membrane was then cut into short strips measuring 4 to 5 mm in width which were then immersed in both patient and normal sera diluted 101 times (10 μl+1,000 μl) with a Tris-buffered saline containing the casein used for blocking. The primary reaction was then carried out at room temperature for 1 hour while shaking. After completion of the primary reaction, the membrane was washed well with a phosphate-buffered saline.

Next, the membrane was immersed in anti-human IgG-peroxidase-labeled antibody (rabbit) diluted 101 times with a Tris-buffered saline containing 0.5% casein. The secondary reaction was then carried out at room temperature for 1 hour while shaking. Following completion of the reaction, a similar washing procedure to that at completion of the primary reaction was performed. A color former [4-chloronaphthol (6 mg/ml) methanol solution/hydrogen peroxide] was then added to the washed membrane to develop color. As a result, a clearly defined, single band having a molecular weight of about 40 KD was detected which was specific to osteoporotic patients.

The method of the present invention is a specific and simple diagnostic method for osteoporosis. Since these autoantigens are extremely well preserved in terms of their evolution, rat tissue antigen is believed to be able to be used in the detection of human osteoporotic autoantibodies in the manner in which human autoantibodies are detected with animal tissue antigens in the diagnosis of collagen diseases, diabetes and other autoimmune diseases. In particular, the fact that mouse antigen reacted to the sera of osteoporotic patients in the same manner as rat antigen in the present invention indicates one example in which autoantigen is evolutionarily well preserved. Moreover, the fact that antibody in the sera of osteoporotic patients reacted strongly with antigen of human squamous cell tongue carcinoma cells indicates that there is antigenic analogy between humans and animals.

As a result of the preserved nature of autoantigens, the tissue sections of not only humans, but also rats, mice and other mammals, or cultured cells of cell lines of mammals demonstrating these antigens, are considered to be able to be used in diagnosis in the same manner as described above. Since the methods described herein using tissue sections are suitable for detection of all types of antibodies to somatic antigens, their range of application is extremely broad. By either extracting and purifying these antigens from tissues, or producing large quantities by cDNA cloning using patient sera as a probe, diagnostic techniques can be developed that are easier and more quantitative than immunofluorescence techniques, examples of which include ELISA, nephrometry, chemiluminescence and radio immuno assay (RIA).

The present invention indicates for the first time the possibility of an autoimmune reaction being intimately involved in the occurrence of osteoporosis. Although this will allow the path to be opened to use of autoantibody detection for diagnosis of osteoporosis, the possibilities are not limited to only this. If osteoporosis is an autoimmune disease, it will be necessary to review at least a portion of the therapeutic methods employed thus far as well as develop completely new therapeutic methods. It will also be of important significance to investigate antibody titers of autoantibodies for the monitoring of these therapeutic methods as well.

What is claimed is:

1. A diagnostic method for human osteoporosis by detecting an antibody in human serum comprising the steps of contacting said human serum with at least one rat or mouse tissue section, said section being epithelium of tongue mucous membrane, epithelium of tracheal mucous membrane, upper lip epidermis or follicular epithelium containing upper lip hair shafts and contacting said at least one tissue section with a secondary immunofluorescent labelled antibody wherein the presence of fluorescence detects osteoporosis.

2. A method of screening a human for osteoporosis, said method comprising:

obtaining serum from said human;

contacting said serum with cultured cells of a human squamous cell tongue carcinoma cell line using cell enzyme-linked immunosorbent assay; and determining which of said serum samples reacts positively in said cell enzyme-linked immunosorbent assay, wherein said positive reaction detects osteoporosis.

3. A method of screening a human for osteoporosis, said method comprising:

obtaining serum from said human;

contacting said serum with an antigen having a molecular weight of about 70 KD or about 40 KD obtained from rat or mouse epithelium of tracheal mucous membrane or an antigen having a molecular weight of about 38 KD obtained from cultured cells of human squamous cell tongue carcinoma cell line SCC-9, the said molecular weight being measured in sodium dodecyl sulfate polyacrylamide gel electrophoresis in the presence of a reducing agent, in an enzyme-linked immunosorbent assay; and determining which of said serum samples reacts positively with said antigen in said enzyme-linked immunosorbent assay, wherein said positive reaction detects osteoporosis.

* * * * *